(12) United States Patent
O'Brien

(10) Patent No.: US 6,733,168 B1
(45) Date of Patent: May 11, 2004

(54) SEPARATING AND SORTING APPARATUS FOR ASPHALT

(76) Inventor: Jack O'Brien, 6 Chenango La., Binghamton, NY (US) 13901

( * ) Notice: Subject to any disclaimer, the term of this patent is extended or adjusted under 35 U.S.C. 154(b) by 78 days.

(21) Appl. No.: 10/128,179

(22) Filed: Apr. 24, 2002

(51) Int. Cl.[7] .................................................. B01F 9/02
(52) U.S. Cl. .............................. 366/4; 366/12; 366/54; 366/147; 366/192; 366/220
(58) Field of Search ................. 366/140, 147, 366/189, 192, 233, 4, 12, 54, 220; 34/130, 394, 395

(56) References Cited

U.S. PATENT DOCUMENTS

| | | | | |
|---|---|---|---|---|
| 1,686,967 A | * | 10/1928 | Harber | 366/99 |
| 3,716,219 A | * | 2/1973 | Miller | 366/60 |
| 4,293,570 A | * | 10/1981 | Vadasz | 426/3 |
| 4,813,154 A | * | 3/1989 | Ronning | 34/395 |
| 5,104,232 A | * | 4/1992 | Lennox, III | 366/227 |
| 5,220,732 A | * | 6/1993 | Lee | 34/393 |
| 5,603,567 A | * | 2/1997 | Peacock | 366/139 |

* cited by examiner

Primary Examiner—Charles E. Cooley
(74) Attorney, Agent, or Firm—Mark Levy & Associates

(57) ABSTRACT

An apparatus and method for testing asphalt in the field is described. The apparatus includes a motor for rotatively driving a chamber containing the asphalt to be tested. The chamber is rotated while cooler, ambient air is circulated through the asphalt particulate. After cooling the particles of the asphalt, the asphalt particles are separated by tumbling action.

18 Claims, 3 Drawing Sheets

SEPARATING AND SORTING APPARATUS FOR ASPHALT

FIELD OF THE INVENTION

The invention relates to field test equipment and, more particularly, to a separating and sorting apparatus and method for treating and processing asphalt particulate in the field.

BACKGROUND OF THE INVENTION

In field tests of asphalt products the separating and sorting of asphalt particulate has always been done by hand. There is no commercial apparatus for doing this, mainly because field-testing is a hands-on, civil engineering trade. The frequency of doing this test, however, warrants something be done to facilitate and/or automate the procedure. Anyone who has ever separated and sorted asphalt can attest to the laborious difficulties encountered in performing this task.

The present invention seeks to provide a new field-testing apparatus to separate and sort asphalt particulate.

The current invention comprises a motor driven, rotating container for holding asphalt. The container has input and output vents for conveying cooler, ambient air through the container, as the asphalt is made to tumble therein. Cooler, ambient air is introduced into the container through the input vent. An electric blower produces the cooler, ambient air, which circulates about the tumbling asphalt particles, causing the particles and liquid asphalt in the asphalt mix to cool. The heat from the mix is discharged through the output vent. The cool, dried-asphalt particles then sink to the bottom of the container, which features a releasable latch. Opening the latch discharges the processed asphalt particulate into a trough disposed below the rotating container. The trough directs the particulate into a receptacle disposed below it.

SUMMARY OF THE INVENTION

In accordance with the present invention, there is provided an apparatus and method for processing asphalt in the field. The apparatus comprises a motor driven rotating container for holding the asphalt to be processed. The container has input and output vents for conveying ambient air through the container as the asphalt is made to tumble therein. Ambient air is introduced into the input vent. An electrically powered blower generates the cooler, ambient air, which circulates about the tumbling asphalt particles causing the components in the asphalt mix to cool, and allowing the hot gases to discharge through the output vent. A baffle plate disposed adjacent the output vent deflects the ambient air and cooler particles from being directed at the field test operator, thus preventing the possibility of burns. The cool, dried asphalt particles sink to the bottom of the container where a spring-loaded latch can be released. Releasing the latch causes the processed asphalt particulate to drop into a trough. The trough gathers the cooled particle portion and then directs it into a receptacle or bucket disposed below the trough.

The process of the invention comprises the steps of: (a) passing cooler, ambient air through the container having asphalt particulate to be processed; (b) tumbling the asphalt particulate while continuing to pass the cooler air through the container to drive off heat; (c) discharging the cooled asphalt particulate into a collecting receptacle. The tumbling action keeps the particles from sticking together as they cool, since at room temperature or below, asphalt particles no longer stick to each other.

It is an object of this invention to provide an apparatus and method for separating and cooling asphalt particulate in the field.

It is another object of the present invention to provide a compact apparatus and method for cooling, field-testing, processing, and separating asphalt particulate.

BRIEF DESCRIPTION OF THE DRAWINGS

A complete understanding of the present invention may be obtained by reference to the accompanying drawings, when considered in conjunction with the subsequent detailed description, in which.

For purposes of brevity and clarity, like components and elements of the apparatus of this invention will bear the same designations or numbering throughout the figures.

DESCRIPTION OF THE PREFERRED EMBODIMENT

Generally speaking, the invention features an apparatus and method for testing asphalt in the field. The apparatus comprises a motor driven chamber containing the asphalt to be tested. The chamber is rotated while cooler, ambient air is circulated through the asphalt particulate. While rotating the particles of the asphalt, the tumbling action causes the asphalt to cool and separate into loose, dry particles.

Figure 1:
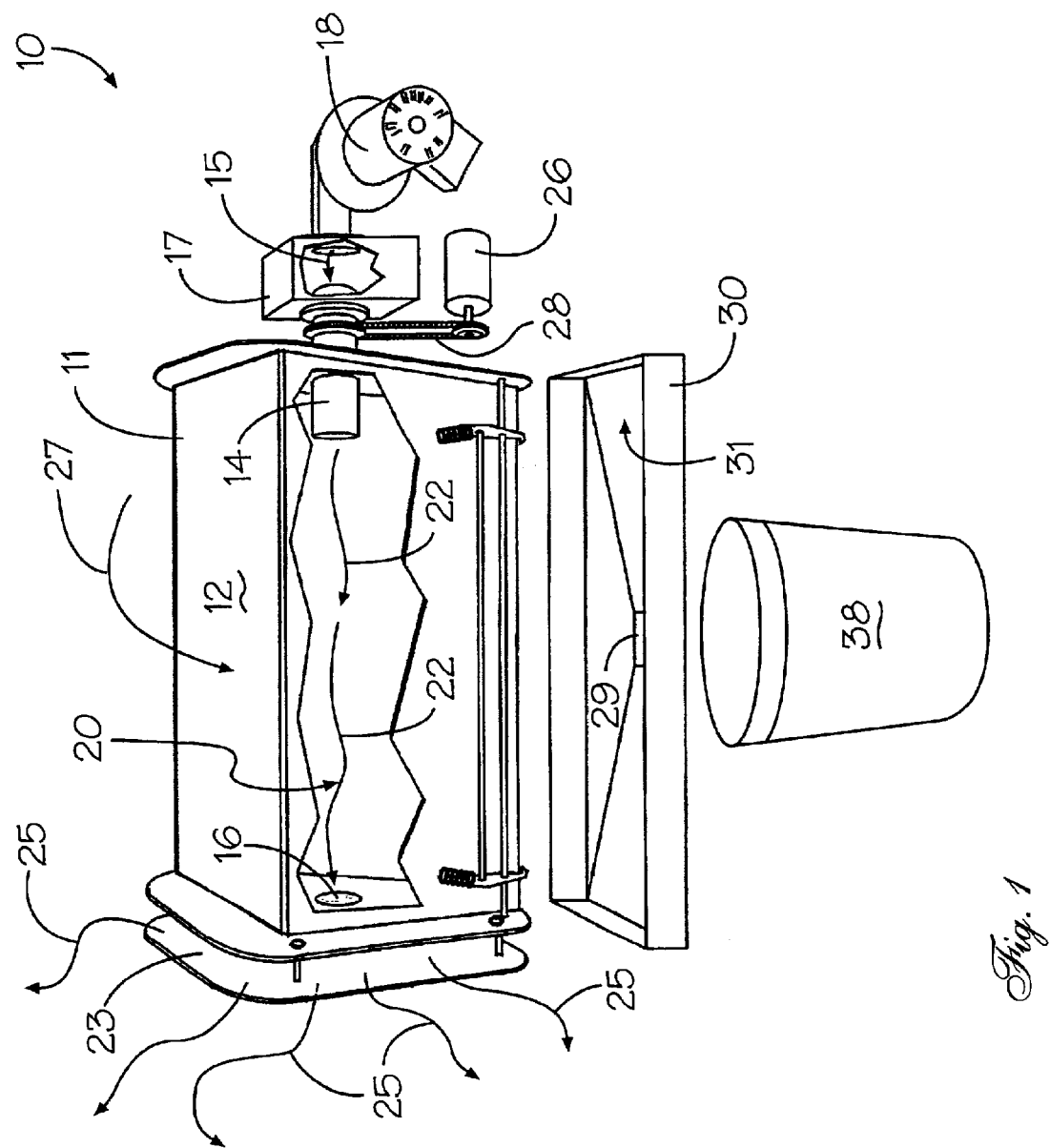
FIG. 1 illustrates a perspective cut-away view of the field-testing apparatus of this invention, shown in a first stage of an asphalt processing procedure.

Now referring to FIG. 1, an apparatus 10 is illustrated for processing asphalt in the field, comprising a container 12 having an inlet 14 and an outlet 16. An electrically operated fan unit 18, comprising an internal fan (not shown), blows cooler, ambient air (arrow 15) into intermediary plenum 17, and connects with the inlet 14. It introduces the cooler, ambient air to the chamber 20, as shown in cut-away view. The cooler air travels (arrows 22) through the chamber 20 and exits through the outlet 16 where it impinges on a baffle plate 23, which disperses the cool air and stray lighter particulate, as shown by arrows 25, in order to prevent burns.

Figure 2:
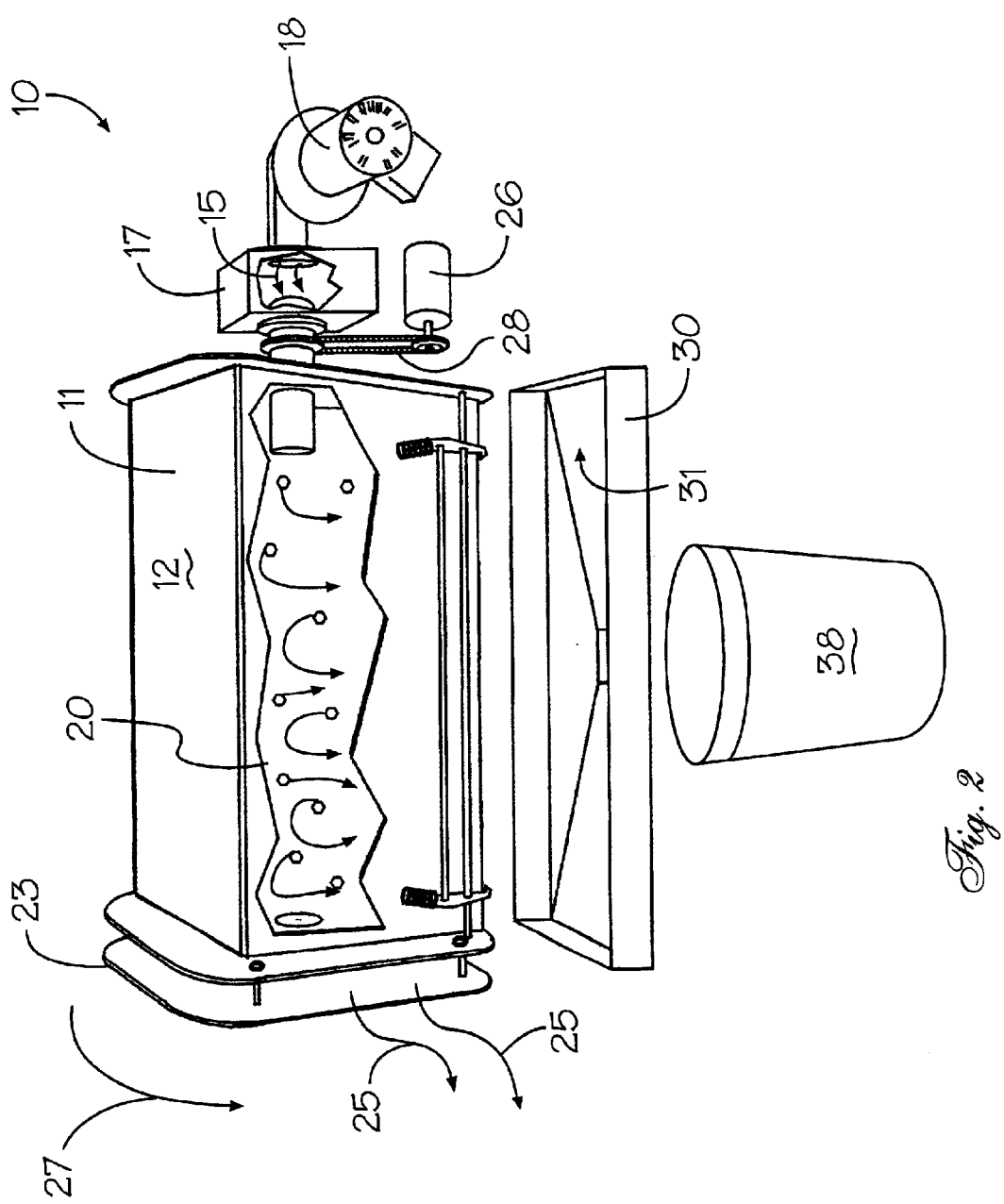
FIG. 2 depicts a perspective view of the field-testing apparatus shown in FIG. 1 in a second stage of an asphalt processing procedure.

The container 12 is rotatably driven (arrow 27) by means of an electric motor 26, operatively connected to the tubular inlet 14, by means of a V-belt, or sprocket and chain transmission system 28. Asphalt to be tested is introduced into the container 12 through the lid 11, as better observed with reference to FIG. 3. Lid 11 is opened (arrow 39), and the asphalt to be tested is poured into chamber 20. The cooler air flowing through the rotating chamber 20 (arrow 27) causes the tumbling asphalt mix to cool, and allows it to remain separate in its component coarse and fine particulate as shown in FIG. 2.

Figure 3:
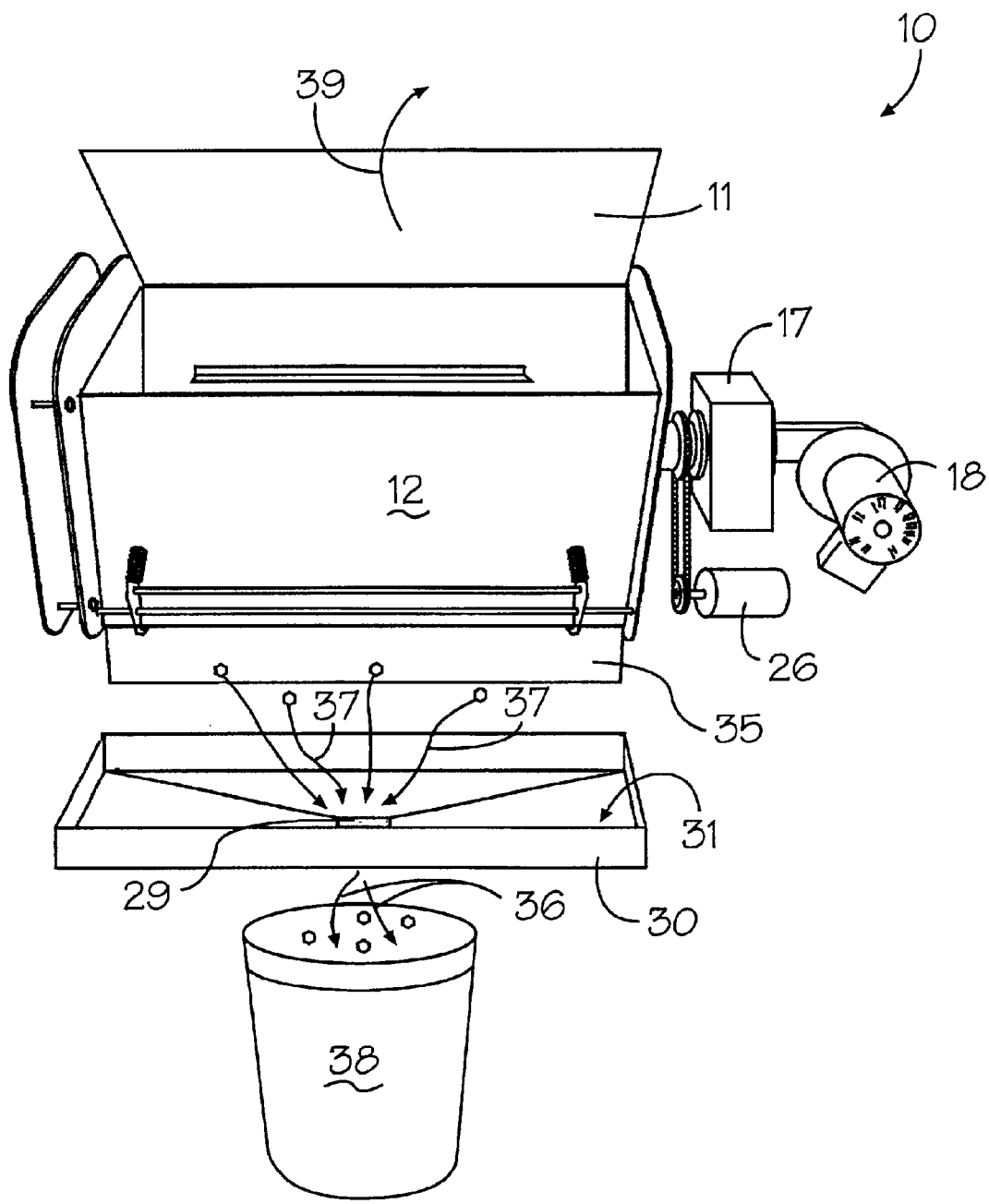
FIG. 3 depicts a perspective view of the field-testing apparatus in a third and final stage of the asphalt processing procedure illustrated in FIGS. 1 and 2.

A second container 30 in the form of a receiving tray is disposed below container 12. The second container 30 has a funnel 29 located in the sloping bottom section 31. Asphalt particulate processed in container 12 will be discharged (arrows 37) to the second container 30 by releasing the spring-biased latch 35 disposed in the bottom of container 12, as depicted in FIG. 3. The asphalt particles are collected (arrows 36) in a bucket or receptacle 38.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by letters patent is presented in the subsequently appended claims.

What is claimed is:

1. A particulate processing apparatus for use in the field, comprising:

an elongated, rotatably driven container having a first openable face disposed substantially parallel to an axis of rotation of said container for receiving a batch of asphalt to be tested, and a second openable face also disposed parallel said axis of rotation for discharging a processed batch of asphalt comprising a separated particulate mix, said container having an inlet and an outlet through which air and hot gases can flow, said particulate mix tumbling within said rotatable container, as said rotatable container is caused to rotate;

cooling means disposed adjacent said rotatable container for cooling air introduced into the inlet of said container, said introduced air processing said particulate mix, and separating the tumbling particulate mix into its component particles by driving off heat within said particulate mix, said cooling air flowing out of said outlet;

collecting means disposed beneath said container adjacent said second openable face for receiving the processed particulate mix from a lower region of said rotatable container; and drive means operatively connected to said container for rotating said container, and for causing the particulate mix to tumble therein.

2. The particulate processing apparatus of claim 1, wherein said air comprises ambient air.

3. The particulate processing apparatus of claim 1, wherein said batch of asphalt comprises liquid bitumen asphaltic cement and aggregate mix.

4. The particulate processing apparatus of claim 1, wherein said drive means comprises one of the group: an electric motor and V-belt transmission; and a chain and sprocket drive.

5. The particulate processing apparatus of claim 1, wherein said cooling means further comprises an electrically operated blower connected to said inlet of said container.

6. The particulate processing apparatus of claim 5, further comprising a plenum disposed between said container and said electrically operated blower.

7. The particulate processing apparatus of claim 1, wherein said collecting means comprises a particulate receiving tray having a funnel disposed therein.

8. The particulate processing apparatus of claim 1, further comprising a baffle plate disposed adjacent said outlet.

9. A method for processing a particulate mix in the field, comprising the steps of:

a) providing a rotatable container having an openable region disposed along a first side thereof and introducing a batch of asphalt to be processed into said openable region;

b) passing cool air through said container holding said batch of asphalt to be processed;

c) tumbling said batch of asphalt while continuing to pass the cool air through the container in order to drive off heat from said batch of asphalt to form a separated particulate mix;

d) discharging cool particulate from a second openable region along a second side of said container into a receptacle; and e) collecting separated coarse particles and finer particles of the processed particulate mix.

10. The method in accordance with claim 9, further comprising the steps of:

f) discharging air from said container; and g) baffling said air that is discharged from said container in step (f).

11. An asphalt particulate processing apparatus for use in the field, comprising:

a rotatably driven elongated container for receiving at an openable region at a first side thereof, processing, and discharging from an openable region along a second side thereof, a batch of asphalt particulate mix, said container having an inlet and an outlet through which fluids can flow, said asphalt particulate mix tumbling within said rotatable container, as it is caused to rotate;

means disposed adjacent said rotatable container for introducing a cooling fluid into the inlet of said container, said introduced fluid processing said asphalt particulate mix, and separating the tumbling asphalt particulate mix into its component particles by driving off heat from said asphalt particulate mix, said fluid flowing out of said outlet;

collecting means disposed adjacent said openable region along a second side of said container for receiving fine and coarse components of said processed asphalt particulate mix; and drive means operatively connected to said container for rotating said container, and for causing the asphalt particulate mix to tumble therein.

12. The asphalt particulate processing apparatus of claim 11, wherein said fluid comprises air.

13. The asphalt particulate processing apparatus of claim 11, wherein said drive means comprises an electric motor and a V-belt transmission disposed between said electric motor and said container.

14. The asphalt particulate processing apparatus of claim 11, wherein said means for introducing a cooling fluid further comprises an electrically operated blower connected to said inlet of said container.

15. The asphalt particulate processing apparatus of claim 14, further comprising a plenum disposed between said container and said electrically operated blower.

16. The asphalt particulate processing apparatus of claim 11, wherein said collecting means comprises a particulate receiving tray having a funnel disposed therein.

17. The asphalt particulate processing apparatus of claim 11, further comprising a baffle plate disposed adjacent said outlet.

18. The asphalt particulate processing apparatus of claim 11, wherein said openable region along a second side of said container comprises a spring-bottom latch in a bottom portion thereof, for discharging processed asphalt particulate.

* * * * *